May 15, 1962 E. S. BOERNER Plant Pat. 2,146
CHRYSANTHEMUM PLANT
Filed May 12, 1961
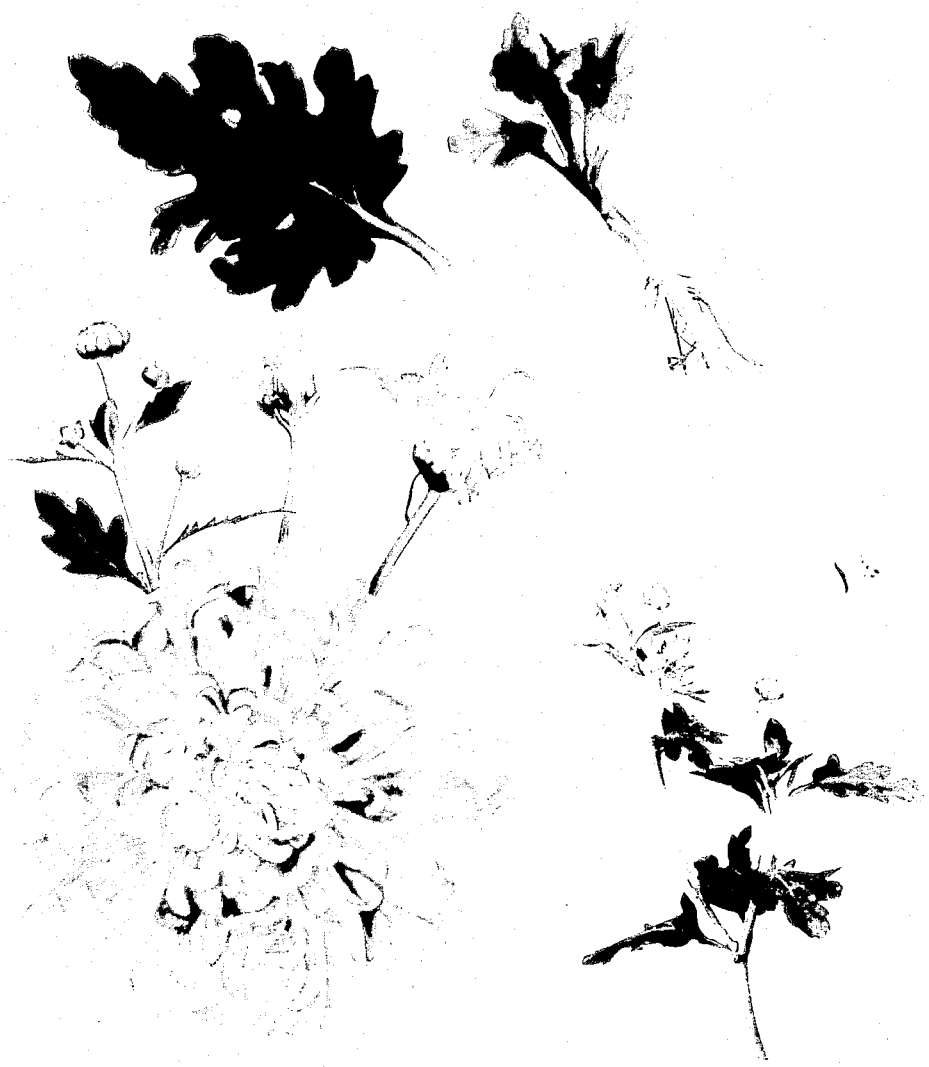
Inventor.
E. S. Boerner
By: Robb & Robb
Attorneys.

United States Patent Office

Plant Pat. 2,146
Patented May 15, 1962

2,146
CHRYSANTHEMUM PLANT

Eugene S. Boerner, Newark, N.Y., assignor to Jackson & Perkins Company, Newark, N.Y., a corporation of New York Filed May 12, 1961, Ser. No. 109,785
1 Claim. (Cl. 47—60)

The present invention relates to a new and distinct variety of chrysanthemum plant of the shaggy incurved type, which was originated by me by crossing an unnamed and unpatented seedling derived from a cross of "Meadow Lark" (Plant Patent No. 1,305)×"Thrush" (Plant Patent No. 1,168) with an unnamed and unpatented large-flowered Hortorum seedling characterized by its golden colored flowers.

The primary objective of this breeding was to produce a new chrysanthemum variety which combines the flower color and vigor of the unnamed seedling parent derived from "Meadow Lark"×"Thrush" with the large flower size and incurved flower type of the Hortorum seedling parent. This objective was fully achieved along with other desirable improvements, as evidenced by the following unique combination of characteristics which are outstanding in the new variety and which distinguish it from its parents, as well as from all other varieties of which I am aware:

(1) A vigorous habit of growth;

(2) Large flower size;

(3) A distinctive oval petal shape in the flowers, with the tips of the petals being cup-shaped; and (4) A distinctive general color tonality of the flowers in which there is a definite color contrast between the inner surfaces of the petals which correspond in color to English Red, and the reverse surfaces of the petals which correspond to Pale Orange Yellow, lightly overcast with Maize Yellow.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, near mid-morning during the latter part of the month of October:

Parentage: Seedling.

*Seed parent.*—An unnamed seedling of "Meadow Lark"×"Thrush."

*Pollen parent.*—An unnamed large-flowered golden colored Hortorum seedling.

Classification: Shaggy; incurved.

Growth: Free.

Cold resistance: Hardy in northern New York State.

Blooming period: From mid-September until frost.

*Flower*

Bud:

*Color.*—When sepals first divide—Rufous, Plate 14. When petals begin to unfurl—Dragon's-Blood Red, Plate 13. When half-blown: inside—Rufous, Plate 14; outside—Pale Orange-Yellow, Plate 3.

*Peduncle.*—Color—Light Cress Green, Plate 31. Strength—strong.

Bloom:

*Size.*—6 inches.

*Stem.*—Strong.

*Form.*—Shaggy; incurved.

*Petalage.*—Double.

*Color.*—Center of flower—Maize Yellow, Plate 4, lightly overcast with Pale Yellow-Orange, Plate 3. Outer petals—Orange Rufous, Plate 2, lightly overcast with Coral Red, Plate 13. Base of petals—Light Greenish Yellow, Plate 5. Inside of petals—English Red, Plate 2. Reverse of petals—Pale Orange-Yellow, Plate 3, lightly overcast with Maize Yellow, Plate 3.

*Petals.*—Texture—thin; crisp. Form—oval, with tips cup-shaped.

*Fragrance.*—Characteristic chrysanthemum.

*Plant*

Form: Upright-branching.

Growth: Very free.

Foliage:

*Size.*—Medium.

*Quantity.*—Heavy.

*Color.*—Upper side—Dark Cress Green, Plate 31. Reverse side—Light Bice Green, Plate 17.

*Texture.*—Leathery.

I claim:

A new and distinct variety of chrysanthemum plant of the shaggy incurved type, substantially as herein shown and described, characterized particularly as to novelty by the unique combination of a vigorous habit of growth, large flower size, a distinctive oval petal shape, with the tips of the petals being cup-shaped, and a distinctive general color tonality of the flowers in which the inside surfaces of the petals correspond in color to English Red, with the reverse surfaces of the petals corresponding to Pale Orange-Yellow, lightly overcast with Maize Yellow.

No references cited.